United States Patent
Kumar

(10) Patent No.: US 11,980,448 B2
(45) Date of Patent: May 14, 2024

(54) APPARATUS AND METHODS OF MONITORING MATERNAL AND FETAL HEART RATE

(71) Applicant: GE Precision Healthcare LLC, Wauwatosa, WI (US)

(72) Inventor: Kiran B. Kumar, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 1001 days.

(21) Appl. No.: 16/553,990

(22) Filed: Aug. 28, 2019

(65) Prior Publication Data

US 2021/0059538 A1 Mar. 4, 2021

(51) Int. Cl.
| | |
|---|---|
| A61B 5/0205 | (2006.01) |
| A61B 5/00 | (2006.01) |
| A61B 5/0531 | (2021.01) |
| A61B 8/00 | (2006.01) |
| A61B 8/02 | (2006.01) |
| A61B 8/08 | (2006.01) |
| G16H 40/63 | (2018.01) |
| A61B 5/024 | (2006.01) |

(52) U.S. Cl.
CPC .......... *A61B 5/0205* (2013.01); *A61B 5/0011* (2013.01); *A61B 5/0531* (2013.01); *A61B 5/4356* (2013.01); *A61B 5/4362* (2013.01); *A61B 5/743* (2013.01); *A61B 5/746* (2013.01); *A61B 8/02* (2013.01); *A61B 8/0866* (2013.01); *A61B 8/4472* (2013.01); *A61B 8/5261* (2013.01); *A61B 8/54* (2013.01); *G16H 40/63* (2018.01); *A61B 5/02411* (2013.01); *A61B 5/02438* (2013.01); *A61B 2562/06* (2013.01)

(58) Field of Classification Search
CPC ... A61B 5/02411; A61B 5/4362; A61B 5/344; A61B 5/4356; A61B 5/0011; A61B 8/0866
See application file for complete search history.

(56) References Cited

U.S. PATENT DOCUMENTS

| | | | |
|---|---|---|---|
| 6,178,343 B1 | 1/2001 | Bindszus et al. | |
| 6,434,418 B1 * | 8/2002 | Neal .................. | A61B 5/02411 600/511 |

(Continued)

FOREIGN PATENT DOCUMENTS

CN 105377143 A 3/2016

OTHER PUBLICATIONS

PCT application PCT/US2020/046620 filed Aug. 17, 2020—International Search Report and Written Opinion dated Oct. 29, 2020; 16 pages.

(Continued)

*Primary Examiner* — Michael J D'Abreu
(74) *Attorney, Agent, or Firm* — Andrus Intellectual Property Law, LLP

(57) ABSTRACT

Systems and methods of maternal and fetal monitoring include acquiring ultrasound physiological data with an ultrasound transducer. A plurality of electrodes acquire biopotential physiological data from the skin of a patient. A controller receives the ultrasound and biopotential physiological data and calculates fetal heart rate (fHR) values, maternal heart rate (mHR) values, and uterine activity (UA) values from the ultrasound and biopotential physiological data.

17 Claims, 4 Drawing Sheets

(56) References Cited

U.S. PATENT DOCUMENTS

| | | | |
|---|---|---|---|
| 6,662,043 B1 | 12/2003 | Shine | |
| 6,740,033 B1* | 5/2004 | Olejniczak | A61B 5/002 |
| | | | 128/903 |
| 7,336,985 B2 | 2/2008 | Wallace et al. | |
| 7,532,923 B1 | 5/2009 | Hayes-Gill et al. | |
| 7,758,522 B2 | 7/2010 | Pandit | |
| 8,229,550 B2 | 7/2012 | James et al. | |
| 8,617,076 B2* | 12/2013 | Kabakov | A61B 8/5276 |
| | | | 600/453 |
| 8,694,081 B2 | 4/2014 | Kabakov | |
| 8,696,578 B2 | 4/2014 | Kabakov et al. | |
| 8,808,203 B2 | 8/2014 | Czarnek | |
| 8,880,140 B2 | 11/2014 | Hayes-Gill et al. | |
| 9,168,022 B2 | 10/2015 | Kabakov et al. | |
| 9,232,929 B2 | 1/2016 | Kabakov et al. | |
| 9,610,060 B2 | 4/2017 | Jaeschke et al. | |
| 9,968,291 B2 | 5/2018 | Hayes-Gill et al. | |
| 2009/0204002 A1 | 8/2009 | Pandit | |
| 2011/0160591 A1 | 6/2011 | Smith et al. | |
| 2016/0120500 A1 | 5/2016 | Myklebust | |
| 2016/0157717 A1* | 6/2016 | Gaster | A61B 5/389 |
| | | | 600/301 |
| 2016/0262649 A1 | 9/2016 | Hayes-Gill et al. | |
| 2017/0049414 A1 | 2/2017 | Venugopalan | |
| 2017/0367643 A1 | 12/2017 | Falk et al. | |
| 2018/0000405 A1 | 1/2018 | Penders | |
| 2018/0317878 A1* | 11/2018 | Wohlschlager | A61B 8/5269 |

OTHER PUBLICATIONS

CN application 202080059746.3 filed Feb. 23, 2022—Office Action issued Aug. 15, 2023; 9 pages.

\* cited by examiner

APPARATUS AND METHODS OF MONITORING MATERNAL AND FETAL HEART RATE

BACKGROUND

The present disclosure relates to maternal and fetal monitoring. More specifically the present disclosure relates to a device and method for monitoring maternal and fetal heart rate.

Prior to the onset of labor, a pregnant patient prefers to be ambulatory. In other words, the pregnant patients prefers to be able to move about freely, whether in the patient's own home or within the hospital. However, a pregnant patient whom is likely to begin labor soon, has reduced ambulatory ability due to the number of sensors that are normally attached to their abdomen to monitor both the onset of labor as well as the health of the unborn baby.

The maternal heart rate can be obtained from the returned ultrasound signals received by the ultrasound transducer. In essence, maternal heart rate may appear as an artifact to the determination of the fetal heart rate. Uterine activity also appears as an artifact to the received ultrasound signal from the ultrasound transducer.

The two most common transducers attached to the pregnant patient during pre-labor and intra labor monitoring are transducers to monitor the fetal heart rate (fHR) and transducers to detect uterine activity (i.e. maternal contractions). Additionally, maternal heart rate is another important parameter to monitor maternal health apart from fetal health. Fetal heart rate is typically monitored by a non-invasive system using a Doppler ultrasound technique to detect a motion of the beating heart of the fetus. The beating heart of the fetus produces a Doppler shift in the ultrasound signal received by the transducer. The Doppler shift frequency is then translated into the fetal heart rate. The uterine activity of the pregnant patient is typically monitored using a separate device known as a tocodynamometer. The tocodynamometer uses pressure or displacement to detect uterine contractions. In one embodiment of a tocodynamometer, a pressure transducer, such as a depressible surface, is affixed to the abdomen of the pregnant patient such that the pressure of the abdomen may be detected, and the contractions monitored. Alternatively, the tocodynamometer may utilize a strain gauge disposed between one or more points affixed to locations on the patient's abdomen, such that the expansion and the contraction of the patient's abdomen may be detected. An advantage of a tocodynamometer is that the detected pressure, displacement, or strain not only provides an indication of contraction onset, but relative strength of the contractions.

Medical devices are known that can be used to detect a fetal electrocardiogram (FECG) without making physical contact with the fetus. Such devices use electrodes that are placed on the mother's skin about the abdomen to detect electro physiological signals. The maternal electrocardiogram (MECG) will also tend to be detected by the electrodes. Uterine activity can also be determined from these electro physiological signals. However, it can be challenging to separate the FECG, MECG and uterine activity from the electro physiological signals and the noise and other artifacts contained therein. One example of such system is Novii wireless patch system available from GE Healthcare.

In addition to the signal processing challenges noted above, biopotential based determinations of fetal heart rate, maternal heart rate, and uterine activity suffer from other challenges as well. The complex signal processing noted above can take time, resulting in a delay in the reporting of the monitored results, such processing exemplarily taking seconds to complete. Additionally, fatty layer of the vernix caseosa around the fetal patient can block or impede the biopotentials from the fetal heart such that fetal ECG is not reliably obtained. Lastly, while biopotential based determinations of uterine activity can be obtained, the relative strength of the contractions, and important parameters in evaluation labor progression, are not obtained from the biopotentials. Therefore, additional solutions in the field of maternal and fetal monitoring are desired.

BRIEF DISCLOSURE

An exemplary embodiment of a maternal and fetal monitoring system includes an ultrasound transducer that acquires ultrasound physiological data. A plurality of electrodes acquire biopotential physiological data from the skin of a patient. A controller receives the ultrasound and biopotential physiological data and calculates fetal heart rate (fHR) values, maternal heart rate (mHR) values, and uterine activity (UA) values from the ultrasound and biopotential physiological data. A graphical display is communicatively connected to the controller and receives and visually presents the calculated fHR values, mHR values, and UA values.

Other embodiments further include the controller calculates first values of fHR, mHR, and UA from the biopotential physiological data and the controller calculates second values of fHR, mHR, and UA from the ultrasound physiological data. The first values or the second values are selected as the calculated fHR values, mHR values, and UA values that are presented on the graphical display. The controller can further calculate a biopotential signal to noise ratio (SNR) from the biopotential physiological data and calculate an ultrasound SNR from the ultrasound physiological data. The controller can select between the first values of fHR, mHR, and UA and the second values of fHR, mHR, and UA based upon the greater of the biopotential SNR and the ultrasound SNR. The controller can also compare the biopotential fHR value, biopotential mHR value, the ultrasonic fHR value and the ultrasonic mHR value to calculate a heart beat coincidence between the mHR values and at least one fHR value.

In additional embodiments, the controller calculates the fHR values, the mHR values, and the UA values using a combination of the ultrasound physiological data and the biopotential data. The controller calculates a biopotential signal to noise ratio (SNR) from the biopotential physiological data and calculates an ultrasound SNR from the ultrasound physiological data. The controller weights the contribution of the biopotential physiological data and the ultrasound physiological data to the calculation of the fHR values, the mHR values, and the UA values based upon the biopotential SNR and the ultrasound SNR.

The plurality of electrodes may be secured within the biocompatible housing. The ultrasound transducer and the plurality of electrodes are held in a fixed position relative to each other within the biocompatible housing. A wireless communication transmitter may be disposed within the biocompatible housing. A wireless communication receiver may be disposed external of the biocompatible housing, wherein either biopotential physiological data and the ultrasound physiological data or the calculated fHR, mHR, and UA, are transmitted from the wireless communication transmitter to the wireless communication receiver. The controller may monitor the biopotential physiological data, detects a leads off condition in the biopotential physiological data, and the controller may operate to instruct the operation of an alarm indicative of a disconnection condition of the ultrasound transducer.

An exemplary embodiment of a method of maternal and fetal monitoring may include acquiring ultrasound physiological data with an ultrasound transducer. Biopotential physiological data is acquired with a plurality of electrodes. Fetal heart rate (fHR) values, maternal heart rate (mHR) values, and uterine activity (UA) values are calculated from the ultrasound and biopotential physiological data.

In methods of maternal and fetal monitoring, a graphical display is operated to visually present the fHR values, mHR values, and the UA values. A transducer is provided with a biocompatible housing to which the ultrasound transducer and the plurality of electrodes are secured. Biopotential fHR values, biopotential mHR values, and biopotential UA values are calculated from the biopotential physiological data. Ultrasonic fHR values, ultrasonic mHR values, and ultrasonic UA values are calculated from the ultrasound physiological data. A heart beat coincidence between the mHR values and at least one fHR value is calculated by comparing the biopotential fHR value, biopotential mHR value, the ultrasonic fHR value and the ultrasonic mHR value. At least one of the biopotential fHR value and the ultrasonic fHR value are identified as a coincident value. The calculation of the coincident value to target fHR is adapted based upon the identification of the coincident value. The coincident values are flagged when stored in the maternal patient's electronic medical record (EMR).

Methods of maternal and fetal monitoring may further include monitoring the biopotential physiological data. A leads off condition may be detected from the monitored biopotential physiological data and an alarm indicative of a disconnection condition of the ultrasound transducer is produced. A voltage may be applied to an electrode of the plurality of electrodes. An impedance is measured in the biopotential physiological data. The leads off condition may be detected based upon the impedance.

DETAILED DISCLOSURE

Figure 1:
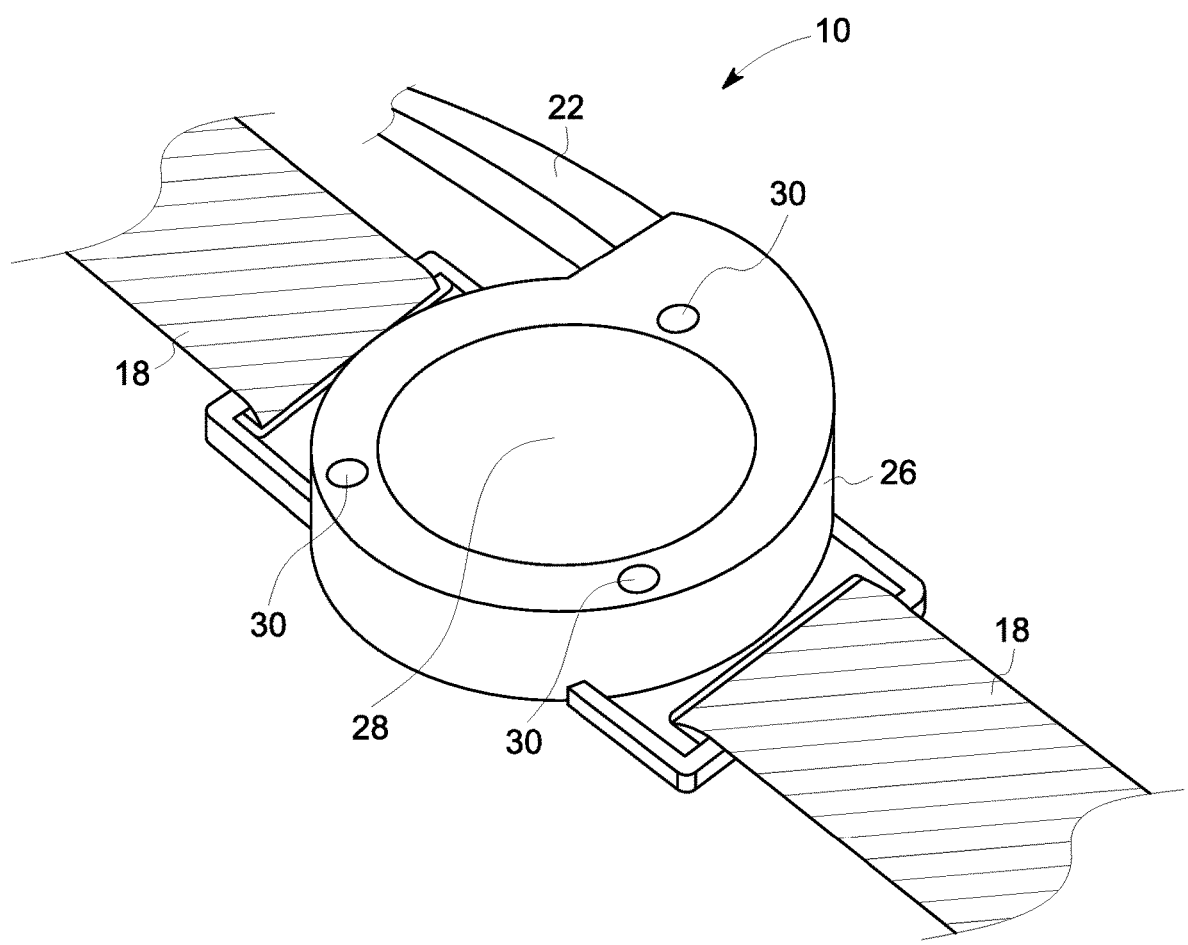
FIG. 1 depicts an exemplary embodiment of a transducer for a maternal and fetal monitor.
Figure 2:
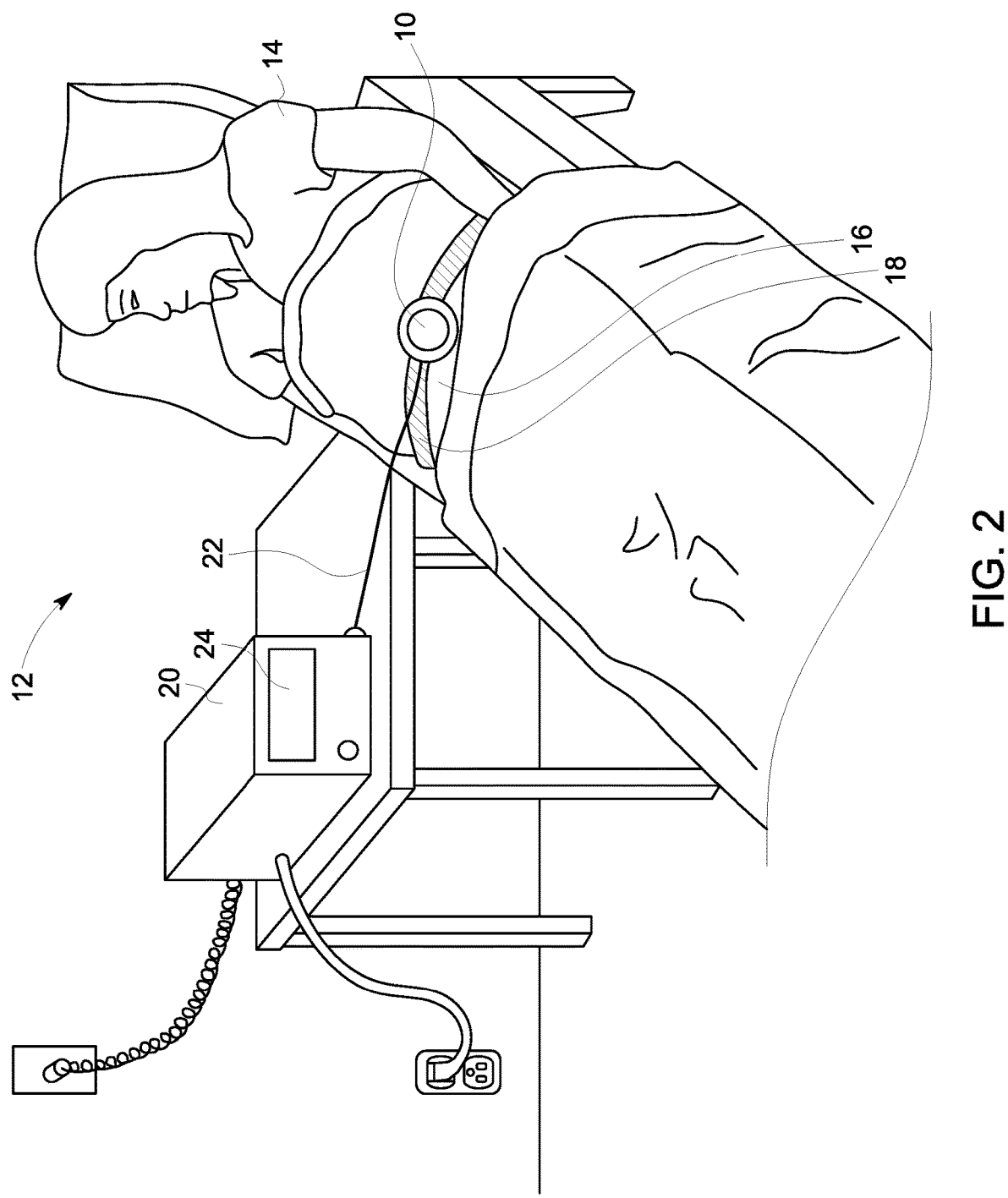
FIG. 2 is a schematic diagram of a maternal and fetal monitor.

FIG. 1 depicts an exemplary embodiment of a transducer 10 as described in further detail herein for use in simultaneously monitoring the health of a maternal patient and fetal patient. FIG. 2 is an environmental view of an exemplary embodiment of a maternal and fetal monitoring system 12 that includes use of the transducer 10. The maternal and fetal monitoring system 12 can be used to simultaneously monitor the heart rates of the maternal patient 14 and the fetal patient within the maternal patient's room.

The transducer 10 is exemplarily secured to the abdomen 16 of the maternal patient 14 for example by way of an elastomeric strap 18. However, it will be recognized that in other embodiments, a biocompatible adhesive may be used to secure the transducer 10 to the patient's abdomen 16.

In embodiments as will be described in further detail herein, the transducer 10 may be communicatively connected to a monitoring device 20 by a communicative connection 22. As will be understood by the variety of implementations as described in further detail herein, while all remaining within the scope of the present disclosure, the communicative connection 22 may exemplarily be a wired or a wireless communicative connection. In still further exemplary embodiments, depending upon the configuration of the maternal and fetal monitoring system and the data transmitted between the transducer 10 and the monitoring device 20, some or all of the data processing of the physiological information acquired the transducer may be performed locally at the transducer 10. A controller located within the transducer may receive the acquired physiological data and process such physiological data in the manners as described herein and the calculated parameters of fHR, mHR, UA or others as described herein may be communicated across the communicative connection 22 to the monitoring device 20 exemplarily for visual presentation on a graphical display 24 and/or electronic storage of this information on a data network of the hospital or medical facility and exemplarily in a electronic medical record (EMR) of the maternal patient.

In other embodiments, the transducer 10 may perform more limited signal processing on the acquired physiological data and provide this physiological data across the communicative connection 22 to a monitoring device 20 which applies the signal processing actions and techniques as described herein to calculate the parameters of fHR, mHR, UA, and others.

Returning back to FIG. 1, the transducer 10 exemplarily includes a housing 26 that encases the electronics of the transducer 10. The transducer 10 includes an ultrasound interface 28. It will be recognized that the ultrasound interface 28 is constructed of an acoustically conductive material and that a plurality of ultrasound crystals are located within the housing 26 behind the ultrasound interface 28. In use, an acoustic enhancing substance which may be a liquid, paste, gel, or solid material may be interspersed between the ultrasound interface 28 and the abdomen of the maternal patient. As will be described in further detail herein, the transducer 10 further includes a plurality of electrodes 30 arranged in the housing 26 on a patient side of the transducer 10 surrounding the ultrasound interface 28. As explained herein, the ultrasound Doppler can be used to determine fHR, mHR, UA, or additionally the ultrasound Doppler can be used to determine fetal movement, FMD.

FIG. 1 depicts three electrodes 30 however, it will be recognized that more or fewer electrodes 30 may be used in other embodiments. In another example, the transducer may include five electrodes 30. As will be described in further detail herein, the electrodes 30 are configured to interface with the skin of the maternal patient and thereby electric biopotentials acquired therefrom these electrical biopotentials including biopotential components from the maternal heart, a fetal heart, and other biopotential sources, including electromyographical (EMG) signals from the maternal and/or fetal patient. In an example, while three electrodes may be sufficient to obtain a measurement of mHR, to obtain other measurement values, additional electrodes may be used. For example, five electrodes may be used when acquiring fHR or UA measurements from biopotentials.

In a non-limiting exemplary embodiment, the electrodes 30 may be constructed from silver and/or silver chloride which may be formed as a foil or a conductive ink for construction of printed electronics. Additionally, at least one of the electrodes 30 may include a plurality of biocompatible conductive needles wherein each needle has a length between 10 micrometers and 200 micrometers. Such needles have been found to assist in providing an improved electric connection, for example by providing micro abrasion of the patient's skin through the stratum corneum to more conductive layers of skin below.

Figure 3:
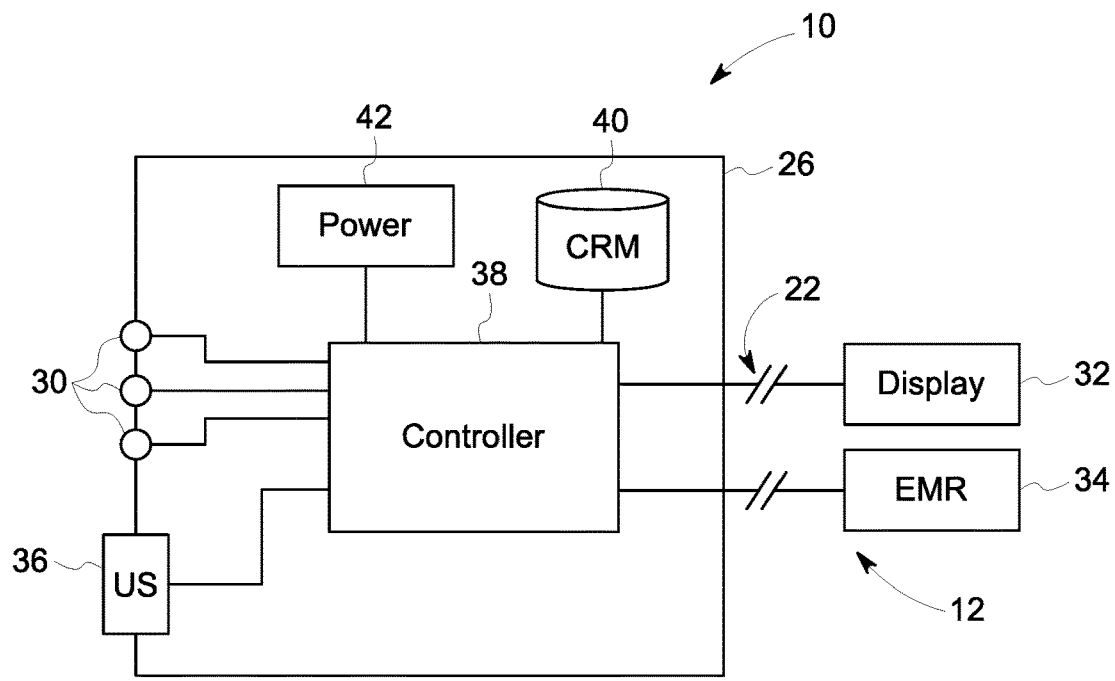
FIG. 3 is a schematic diagram of a maternal and fetal monitor.

FIG. 3 is schematic diagram of an exemplary embodiment of a maternal and fetal monitoring system 12 in which the transducer 10 performs the primary calculations of physiological parameters prior to transmission from the transducer 10 across a communicative connection 22 for visual presentation on a graphical display 32 or storage in an electronic medical record 34 stored on a non-transient computer readable medium within the a hospital or medical care system's information network.

As shown in FIG. 3, contained within the housing 26 of the transducer 10 are the electrodes 30 and an ultrasound transducer 36. The ultrasound transducer 36 exemplarily includes a plurality of ultrasound crystals. When the ultrasound crystals receive a suitable excitation signal, the ultrasound crystals of the ultrasound transducers 36 produce an acoustic wave therefrom. In an example, the excitation signal delivered to the ultrasound transducer 36 is a 6 volt peak-to-peak sign wave at 1.15 MHz. In a further exemplary embodiment, the 1.15 MHz sign wave produces a brief burst frequency from the ultrasound crystals between 2 kHz-4 kHz. These examples are merely exemplary of the values for the excitation signal and the ultrasound crystal burst frequency and those of ordinary skill in the art will recognize many other values may be used in clinical citing's with the excitation signal and the ultrasound burst frequency being coordinated to produce a desirable signal from the ultrasound transducer. In operation, the ultrasound crystals serve as both ultrasound transmitters and ultrasound receivers and the ultrasound transducer 36 is operated to produce the acoustic wave form as described and then operated in a receive mode to receive the returned reflected acoustic signals back at the ultrasound transducer 26. The acoustic signals produced by the ultrasound transducer 36 reflect off of the anatomical structures of the maternal and fetal patients, particularly at the surfaces of transition between biological tissues of varying acoustic property.

The electrodes 30 and the ultrasound transducer 36 are connected to a controller 38. It will be recognized that the controller 38 is exemplarily any of a variety of known controller circuits, integrated circuits, micro controllers, micro processors, and associated circuitry. The controller 38 may exemplarily include a central processing unit (CPU) and integrated memory, although in embodiments the computer readable medium 40 comprising the memory may be a separate component or communicatively connected to the controller 38 within the transducer 10. The controller exemplarily includes a processor that accesses software or firmware in the form of computer readable code stored on non-transient computer readable medium as either integrated memory or external memory. The processor executes the computer readable code as an instruction set to carry out the functions as described herein, including the receipt of input, calculations, and outputs as will be described.

The transducer 10 further includes a power source 42 the power source 42 is exemplarily a battery. While not so depicted herein, it will be recognized that the controller 38 may provide operational control signals to a wave form generator (not depicted) to produce the aforementioned excitation signals for operation of the ultrasound transducer 36. Additionally, it will be recognized that suitable preprocessing circuitry may be positioned between the electrodes 30 and the ultrasound transducer 36 and the controller 38. Such suitable pre-processing circuitry may exemplarily include an analog to digital converter and initial amplification and/or filter circuitry as may be needed to provide a suitable digital input to the controller 38.

Figure 4:
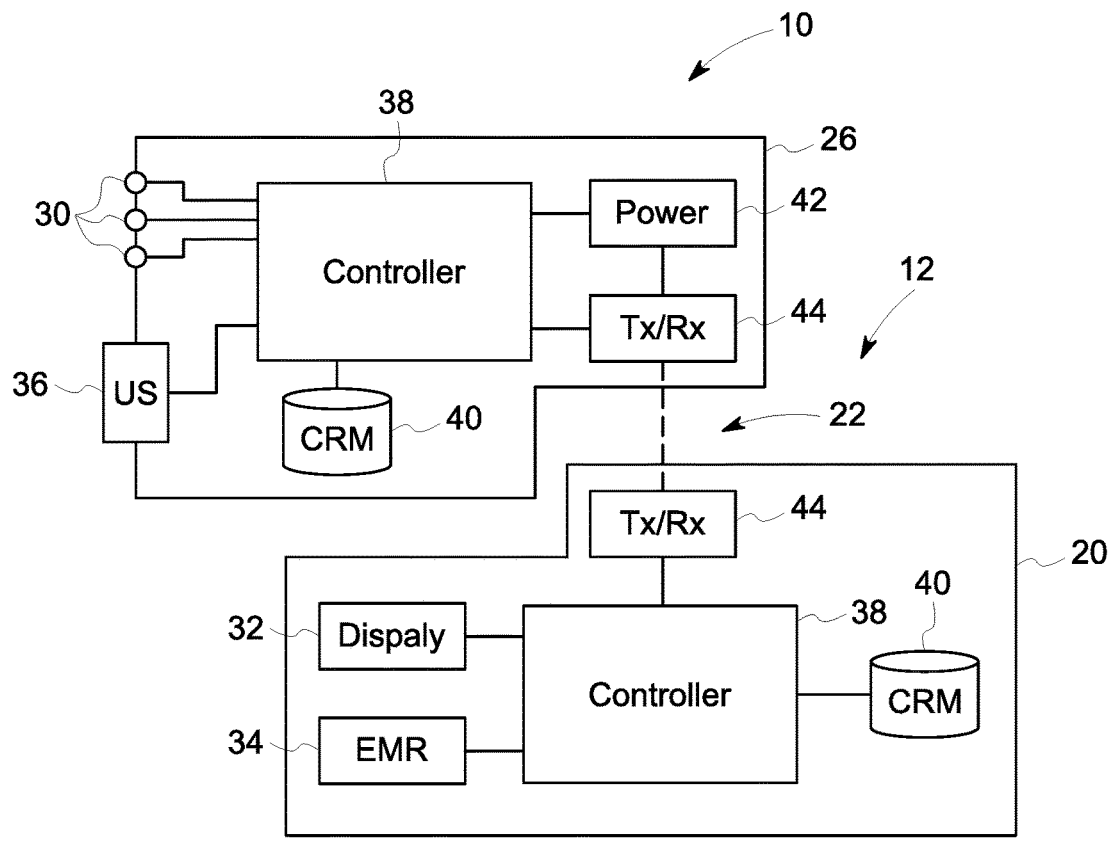
FIG. 4 is a flow chart that depicts and exemplary embodiment of a method of maternal and fetal monitoring.

FIG. 4 also depicts the maternal and fetal monitoring system 12 but does so in an implementation in which the transducer 10 collects to physiological data from the patient and performs preprocessing on the physiological data but instead transmits the collected physiological through the communicative connection 22 provided by a pair of transmit and receive units 44 to a local monitoring device 20 for processing and calculation of the physiological parameters of the maternal and fetal patient. In the implementation of the maternal and fetal monitoring system 12. As shown in FIG. 4, the controller 38 of the transducer 10 may exemplarily include preprocessing filtering, amplification and AD conversion in addition to preparing the physiological data for transmission along the communicative connection 22. Such communicative connection 22 may exemplarily be a wired or wireless communicative connection. In the wireless communicative connection shown in FIG. 4, may exemplarily use Wifi, Bluetooth, or ZigBee communication protocols or other RF communication protocols as may be recognized by a person of ordinary skill in the art. Other forms of wireless communication, including, but not limited to, optical may also similarly be used. The controller 38 exemplarily includes the components necessary for processing the physiological data for transmission, including, but not limited to modulation, using a carrier frequency for data transmission.

The monitoring device 20 receives the transmitted physiological data and performs the signal processing as described in further detail herein to calculate the physiological data and other controls in response to the received physiological data.

Figure 5:
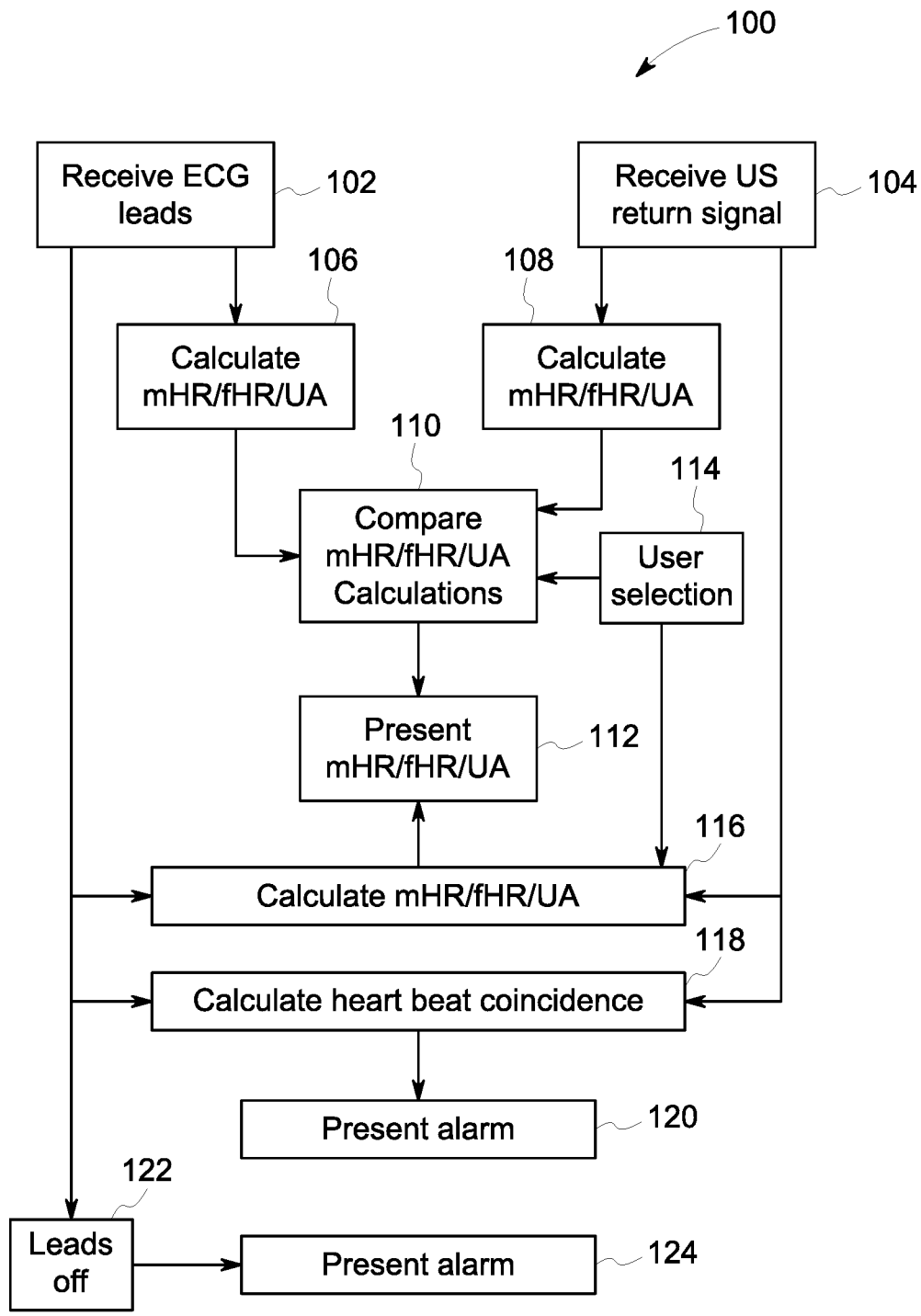
FIG. 5 is a flow chart that depicts an exemplary embodiment of a method 100 of monitoring maternal and fetal patients.

FIG. 5 is a flow chart that depicts an exemplary embodiment of a method 100 of monitoring maternal and fetal patients. The method 100 as described herein exemplarily can be performed by the execution of an instruction set of software embodied in computer readable code that is accessed and executed by the CPU of the controller 38 as described above in response to the receipt of the acquired physiological data. At 102, electrocardiographic leads are received. In exemplary embodiments, the ECG leads are the voltage differentials between two or more of the electrodes on the transducer. In such embodiments, the voltage potential at one of the electrodes is the reference potential to which the other electrode potentials are compared. The generation of the leads may be done in an analog implementation or in a digital implementation. It will be understood that in examples, the electrodes acquire all available biopotentials at the patient's skin. Furthermore, in addition to ECG, EMG or other measurement values may also be isolated from these collected biopotentials.

At 104, the ultrasound return signal is received at the controller from the ultrasound transducer. The returned ultrasound signal is exemplarily acquired by coordinated switching of the individual ultrasound crystals between transmit and receive operations.

With the receipt of the ECG leads and the ultrasound returned signal, the method can operate in two manners dependent upon operation selections or user preferences. In one operation at 106, the mHR, fHR, and UA are calculated from the biopotentials of the received ECG leads. In an exemplary and non-limiting embodiment, the mECG is typically a stronger signal typically in the range of 1,000-5,000 micro volts. Therefore, in one embodiment, the maternal ECG is first identified and extracted from the ECG leads and the fECG signal which may typically be between 0.1 and 40 micro volts may be calculated from the remaining signal. UA can be calculated using a block or moving window average of the received biopotential with low pass filtering and/or band pass filtering of low frequency (e.g. less than 1 Hz). This filtering can isolate the EMG excitation of the abdominal muscles of the maternal patient.

At 108, the returned ultrasound signals can be used to calculate mHR, fHR, and UA in the manners as exemplarily known in ultrasound fetal monitoring based upon Doppler shift in the returned ultrasound signals. It will be recognized, however, that due to the manner of heart rate detection, that Doppler shift based calculations of mHR and fHR are average heart rates over a plurality of heart beats, rather than writing the capability of instantaneous beat-to-beat heart rates as obtainable from electrocardiogram analysis.

At 110, the mHR, fHR, and UA calculations based upon the ECG data and based upon the returned ultrasound data are compared and a selection is made between the calculated values. In an exemplary embodiment, this comparison at 110 may further include the calculation of a signal quality of the input biopotential data and the returned ultrasound signal data in evaluating the calculations to be selected. Such comparison may include the calculation of a signal to noise ratio (SNR) of the respective physiological data. In an exemplary embodiment, SNR may be calculated as the ratio of an average or an expected value of the incoming signal to an estimate of the standard deviation of the noise in such signal. However, persons of ordinary skill in the art will recognize other manners in which SNR may be calculated. In other implementations, the comparison at 110 may result in switching between the two calculations based upon the current conditions of the signals. In exemplary embodiments, movement of the fetus and/or movement of the transducer may result in one or the other of the ECG based or ultrasound based calculations being determined to be the selected calculation for presentation at 112. In a still further embodiment, the selection may include one or more of the ECG based calculations and one or more of the ultrasound based calculation if the determined quality thereof yields the highest quality outputs.

In a still further exemplary, at 114 a user selection may be received either by way of a user input or a previously stored user preference whereby a specific selection in of the manner in which the maternal heart rate, fetal heart rate, and uterine activity are calculated. In one example, a clinician may want an output of instantaneous beat-to-beat heart rate of the maternal patient and therefore make a selection to operate the calculations based upon the ECG data as opposed to the average heart rate calculated based upon the ultrasound data.

As previously noted, the selected calculations of maternal heart rate, fetal heart rate, and uterine activity may be presented at 112, for example on a graphical display. It will also be recognized that these calculation may be recorded at a non-transient computer readable medium, for example as a part of a patient's electronic medical record.

In an additional optional implementation, the combined physiological data of the received ECG data and the received returned ultrasound data are used to produce the output values of mHR, fHR, and UA. The combined use of the ECG and ultrasound data to calculate mHR, fHR, and UA may exemplarily improve the overall quality of the determinations produced as the physiological data of the ECG biopotentials and the ultrasound Doppler information may be complimentary in their processing whereby specific beat-to-beat occurrences determined from the ECG data, exemplarily of the mothers heart may be used to improve the analysis of the ultrasound Doppler analysis by providing a timing of the maternal heart beats. Therefore, in embodiments the calculation of mHR, fHR, and UA at 116 based upon the ECG biopotential data and the ultrasound data may be the preferred calculation for the presented physiological values of mHR, fHR, and UA at 112. This preference may be established by the user selection at 114. As a further user selection at 114, the method 100 may progress to calculate the mHR, fHR, and UA at 116 based upon the ECG data and the ultrasound data unless, a determination is made that one of the data sources is of low quality, for example, based upon signal to noise ratio or loss of an identified contribution to mHR, fHR, or UA calculations from that data source at which point the method may switch to calculation at 106 or 108 based solely upon the available data or the calculation at 116 may be weighted to place more reliance upon the determined higher quality of input physiological data.

At 116 the inputs of ECG data received at 102 and the ultrasound data received at 104 are used. Similarly at 106 and 108, the inputs of the ECG data and the ultrasound data are used. In examples, the calculations at 116 differ from those at 106 and/or 108 as the calculations at 116 use a combination of the ECG data and the ultrasound data to calculate values of each of MHR, fHR, or UA, while in 106 and 108, the calculations of each of those physiological parameters are performed from a single modality (ECG or ultrasound) and those separate calculated values used or selected from, for example based upon a quality of signal in terms of signal to noise ratio.

In addition to the advantages presented in the method 100 herein for the calculation and presentation of mHR, fHR, and UA in maternal and fetal patient monitoring, the transducer of combined biopotential data and ultrasound data can provide further advantages in the method 100. At 118, the ECG data received at 102 and the ultrasound data received at 104 can be used to calculate a heart beat coincidence (HBC). Heart beat coincidence refers to the error in maternal and fetal physiological monitoring in which there is a tendency for the maternal physiological signal (more specifically heart beat) to overwhelm the fetal physiological activity and whereby the calculation of fetal heart rate instead calculates the heart beat of the mother instead of the fetus therefore, a check on the calculated fHR is desirable to ensure that the calculated fHR is not over influenced by the maternal heart beat.

As a first example, HBC may be calculated between fHR as obtained from the Doppler ultrasound and mHR as obtained from the ECG leads acquired from the electrodes. In other examples, the combined physiological data of the ECG data and the ultrasound data provide two different measurements of the maternal and fetal heart beats with the ECG calculation based upon the electrical activity of the fetal and maternal hearts while the ultrasound data provides a calculation based upon the mechanical motion as a result of the fetal and maternal heart beats. Therefore, by comparing the maternal and fetal heart rates for example as calculated at 106 not only with each other, but with the calculations of maternal and fetal heart rate calculated at 108, an improved calculation of heart beat coincidence can be made. HBC can be calculated in different manners. HBC can be based upon a time and phase of peak detection, for example when comparing MECG with FECG. In another example, HBC can be based upon first calculating mHR and fHR from any modality channel and then comparing the respective calculated values of mHR and fHR.

In an example, the determination of HBC may further identify wherein one of the fetal heart rate calculations suffers from heart beat coincidence while the other calculation does not. This may exemplarily be identified if three of the four calculations of fetal and maternal heart rates are the same or coincident while one calculation of fetal heart rate is different. The coincidence may be defined as a 1:1 correspondence between the calculated heart beats and/or calculated heart rate, although in other embodiments it will be recognized that such one-to-one correspondence may be provided with a margin of error and not necessarily require a literal 1:1 ratio.

Upon the identification of heart beat coincidence at 118, then at 120 an alarm or an alert of heart beat coincidence is produced at 120. The alarm may be visually presented on the graphical display and/or may take the form of a flag to invitation in the calculated fHR values. In addition to the alarm at 120, the calculation of fHR may be modified upon the detection of heart beat coincidence in order to rectify this occurrence. In an exemplary response, a filter to remove the maternal heart beat signal from the physiological data may be adapted to help improve the isolation of the fetal heart beat in the physiological data.

In a still further feature of the method 100, at 122 the electrical signals collected from the electrodes may further be used to provide a detection of a leads off condition of the electrodes, and thereby indicate a poor interface between the transducer 10 and the skin of the maternal patient. In one example, the electrodes may be provided with an applied voltage and an impedance across the electrodes calculated. As the electrical circuit is between the electrodes is completed through the skin of the maternal patient, a leads off condition represents an open circuit and a high impedance. Since an ultrasound transducer still recollects a returned acoustic signal, it is difficult to determine purely based upon an ultrasound signal whether the ultrasound transducer has become disconnected from the skin of the maternal patient or if the transducer and/or the fetus have moved relative to one another resulting in a reduction in signal quality. The additional confirmation of a leads off determination at 122 can result in an alarm 124 which may be visibly presented or audibly presented and may provide a clinician with an indication that the transducer 10 must be either reconnected or repositioned relative to the abdomen of the maternal patient.

In a still further exemplary embodiment, with the detection of fHR and mHR from two different physiological properties (e.g. biopotential and mechanical motion), a comparison between these two determinations can be made to further evaluate fetal and/or maternal health. By comparing the onset and occurrence of heart beats as detected based upon the electrical activity against the onset and occurrence of heart beats as detected based upon mechanical motion, discontinuities between these two physiological observations can be detected. As an example, discontinuity between electrical impulses and the expected mechanical motion to result from such electrical impulses can be observed. Detection of this anomaly can provide an early warning of serious medical conditions. In a still further exemplary embodiment, an estimate of maternal blood pressure can be calculated through a comparison of two different determinations of maternal pulse rate.

In exemplary embodiments as disclosed herein, because two different determinations of maternal heart rate are provided, embodiments as disclosed herein may enable a clinician to monitor the maternal and fetal patients without the use of a separate $SPO_2$ sensor. $SPO_2$ sensors are typically worn as stand alone devices secured to an extremity of the maternal patient, for example a finger. As noted above, a pregnant patient may desire relatively unimpeded and elation or movement during labor and thus elimination of a separate $SPO_2$ transducer may provide patient comfort and one fewer transducer for monitoring by the attending clinician.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of maternal and fetal monitoring, the method comprising:
    acquiring ultrasound physiological data with an ultrasound transducer and biopotential physiological data with a plurality of electrodes, from a maternal patient and a fetal patient, wherein the ultrasound transducer and the plurality of electrodes are encased in a housing, the housing configured to be positioned on the maternal patient abdomen;
    calculating biopotential fetal heart rate (fHR) values, biopotential maternal heart rate (mHR) values, and biopotential uterine activity (UA) values from the biopotential physiological data with a controller; and calculating ultrasonic fHR values, ultrasonic mHR values, and ultrasonic UA values from the ultrasound physiological data with the controller;

comparing at least a signal quality of ultrasonic and biopotential fHR values, mHR values, and UA values and based on the comparison selecting fHR values, mHR values, and UA values to be displayed with the controller;

operating a graphical display to visually present the selected fHR values, mHR values, and the UA values.

2. The method of claim 1, further comprising calculating heart beat coincidence by comparing the biopotential fHR value, biopotential mHR value, the ultrasonic fHR value and the ultrasonic mHR value to calculate a heart beat coincidence between the mHR values and at least one fHR value, wherein the step of selecting the fHR values, the mHR values, and the UA values to be displayed is based on the heart beat coincidence.

3. The method of claim 2, further comprising identifying a coincident value for at least one of the biopotential fHR value and the ultrasonic fHR value.

4. The method of claim 3, further comprising adapting the calculation of the coincident value to a target fHR.

5. The method of claim 3, further comprising flagging the coincident value when stored in the maternal patient's electronic medical record (EMR).

6. The method of claim 1, further comprising:
monitoring the biopotential physiological data;
detecting a leads off condition; and
producing an alarm indicative of a disconnection condition of the plurality of electrodes.

7. The method of claim 6, further comprising:
applying a voltage to an electrode of the plurality of electrodes;
measuring an impedance in the biopotential physiological data;
detecting the leads off condition based upon the impedance.

8. The method of claim 1, further comprising providing a transducer with a biocompatible housing to which the ultrasound transducer and the plurality of electrodes are secured.

9. The method of claim 1, further comprising calculating a biopotential signal to noise ratio (SNR) from the biopotential physiological data and calculating an ultrasonic SNR from the ultrasound physiological data; and
wherein the selection of the ultrasonic fHR values or the biopotential fHR values is based on the biopotential SNR and the ultrasonic SNR and/or the selection of the ultrasonic mHR values or the biopotential mHR values is based on the biopotential SNR and the ultrasonic SNR.

10. The method of claim 1, wherein the selected fHR values are the ultrasonic fHR values or the biopotential fHR values, the selected mHR values are the ultrasonic mHR values or the biopotential mHR values, and selected UA values are the ultrasonic UA values or the biopotential UA values.

11. A maternal and fetal monitoring system comprising:
an ultrasound transducer configured to acquire ultrasound physiological data from the maternal patient and a fetal patient;
a plurality of electrodes configured to acquire biopotential physiological data from the maternal patient and the fetal patient;
a housing encasing the electronics of the ultrasound transducer and the plurality of electrodes, the housing configured to be positioned on the maternal patient abdomen;
a controller that receives the ultrasound and biopotential physiological data and calculates first fetal heart rate (fHR) values, first maternal heart rate (mHR) values, and first uterine activity (UA) values from the biopotential physiological data and second fHR values, second mHR values, and second UA values from the ultrasound physiological data;
wherein the controller compares at least a signal quality of first and second fHR values, mHR values, and UA values and based on the comparison selects fHR values, mHR values, and UA values to be displayed; and
a graphical display communicatively connected to the controller to receive and visually present the selected fHR values, mHR values, and UA values.

12. The system of claim 11, further comprising a biocompatible housing, wherein the ultrasound transducer and the plurality of electrodes are secured within the biocompatible housing.

13. The system of claim 12, wherein the ultrasound transducer and the plurality of electrodes are held in a fixed position relative to each other within the biocompatible housing.

14. The system of claim 13, further comprising:
a wireless communication transmitter disposed within the biocompatible housing; and a wireless communication receiver disposed external of the biocompatible housing, wherein either biopotential physiological data and the ultrasound physiological data or the selected fHR, mHR, and UA, are transmitted from the wireless communication transmitter to the wireless communication receiver.

15. The system of claim 11, wherein the controller further calculates a biopotential signal to noise ratio (SNR) from the biopotential physiological data, calculates an ultrasound SNR from the ultrasound physiological data; and
wherein the comparison and selection between the first values and the second values is based upon the greater of the biopotential SNR and the ultrasound SNR.

16. The system of claim 11, wherein the controller further compares the biopotential fHR value, biopotential mHR value, the ultrasonic fHR value and the ultrasonic mHR value to calculate a heart beat coincidence between the mHR values and at least one fHR value; and
wherein the comparison and selection between the first values and the second values is based upon the heart beat coincidence between the mHR values and at least one fHR value.

17. The system of claim 11, wherein the controller monitors the biopotential physiological data, detects a leads off condition in the biopotential physiological data, and the controller operates to instruct the operation of an alarm indicative of a disconnection condition of the ultrasound transducer.

* * * * *